United States Patent
Sagstetter et al.

[19]

[11] Patent Number: 5,957,125
[45] Date of Patent: Sep. 28, 1999

[54] APPARATUS FOR INDICATING PROPER ORIENTATION FOR ORAL AND NASAL INHALERS

[75] Inventors: William E. Sagstetter, Denver; Ewan Grantham; Alan A. Wanderer, both of Castle Rock, all of Colo.

[73] Assignee: Medical Safety Products, Inc., Englewood, Colo.

[21] Appl. No.: 08/963,880

[22] Filed: Nov. 4, 1997

Related U.S. Application Data

[60] Provisional application No. 60/030,212, Nov. 5, 1996.
[51] Int. Cl.$^6$ .............................. A61M 11/00; A62B 7/00
[52] U.S. Cl. .................................. 128/200.23; 128/205.23
[58] Field of Search ......................... 128/205.23, 200.23, 128/203.15; 341/27; 164/150.1; 116/215, 227, 264; 33/379, 365; 239/71, 73, 338; 73/1.75; 222/155, 156, 635

[56] References Cited

U.S. PATENT DOCUMENTS

| | | | |
|---|---|---|---|
| 1,995,919 | 6/1935 | Genung | 116/215 |
| 2,617,381 | 4/1952 | Insul | 116/215 |
| 3,404,681 | 10/1968 | Fowler | 128/173 |
| 4,291,688 | 9/1981 | Kistler | 128/200.23 |
| 4,438,720 | 3/1984 | Conn | 116/215 |
| 5,349,945 | 9/1994 | Wass et al. | 128/200.14 |
| 5,355,873 | 10/1994 | Del Bon et al. | 128/200.23 |
| 5,363,842 | 11/1994 | Mishelevich et al. | 128/200.14 |

FOREIGN PATENT DOCUMENTS

95/26212   10/1995   WIPO .......................... A61M 15/00

OTHER PUBLICATIONS

"What do Pediatricians in Training Know About the Correct Use of Inhalers and Spacer Devises?" J. Allergy Clin. Immunol. 94: 669.

*Primary Examiner*—John G. Weiss
*Assistant Examiner*—Todd M. Martin
*Attorney, Agent, or Firm*—Dorr, Carson, Sloan & Birney, P.C.

[57] ABSTRACT

The present apparatus insures proper orientation during use of an oral or nasal inhaler, as well as providing an audible rattle to aid in remembering to shake the inhaler prior to use. An indicator ball is confined within a substantially horizontal tube in the inhaler housing. One end of the tube is visually exposed within the user's field of view. The indicator ball remains out of view within the inhaler housing unless the inhaler orientation is held in a substantially vertical orientation. When proper vertical orientation is achieved, the indicator ball rolls to the exposed end of the tube and is visible to the user. Shaking the inhaler prior to use causes the indicator ball to rattle within the tube producing an audible rattle. The event of shaking the inhaler and hearing the rattle provides the user with a reinforced memory to shake the inhaler prior to use. In the preferred embodiment as applied to oral inhalers, the indicator ball and tube are placed within an ergonomic cap seated on the upper end of the aerosol vial of the inhaler. When the inhaler mouthpiece is placed in or adjacent to the mouth, the cap and the exposed end of the tube are proximate to the bridge of the nose, directly between the user's eyes. The cap can be equipped with a top surface curved to fit the contour of the first finger knuckle. This improves leverage and reduces stress on the finger when using the inhaler. In the preferred embodiment as applied to nasal inhalers, the indicator ball and tube are placed within a collar housing placed upon the inhaler.

25 Claims, 7 Drawing Sheets

Fig. 6
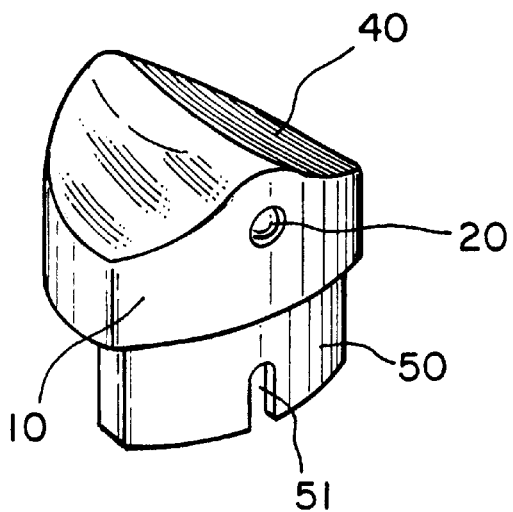
Fig. 5
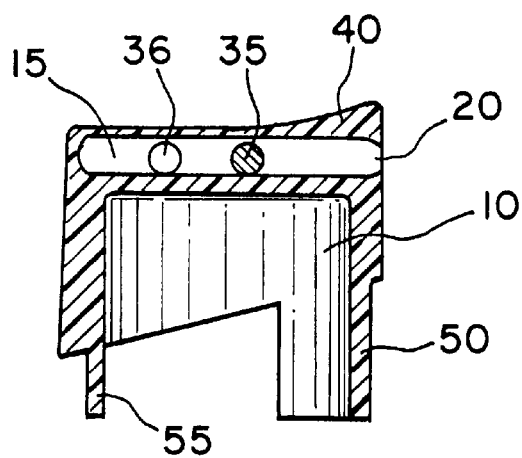
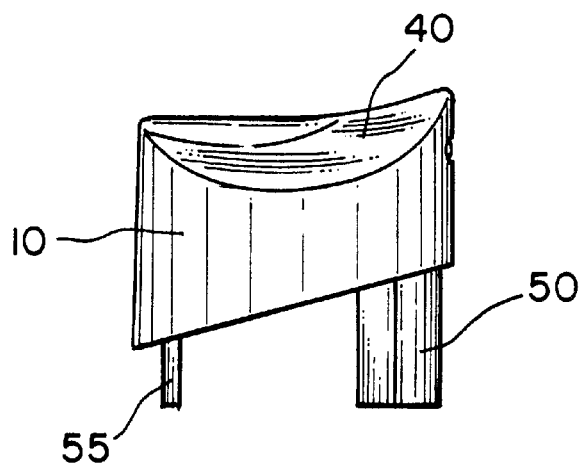
Fig. 7

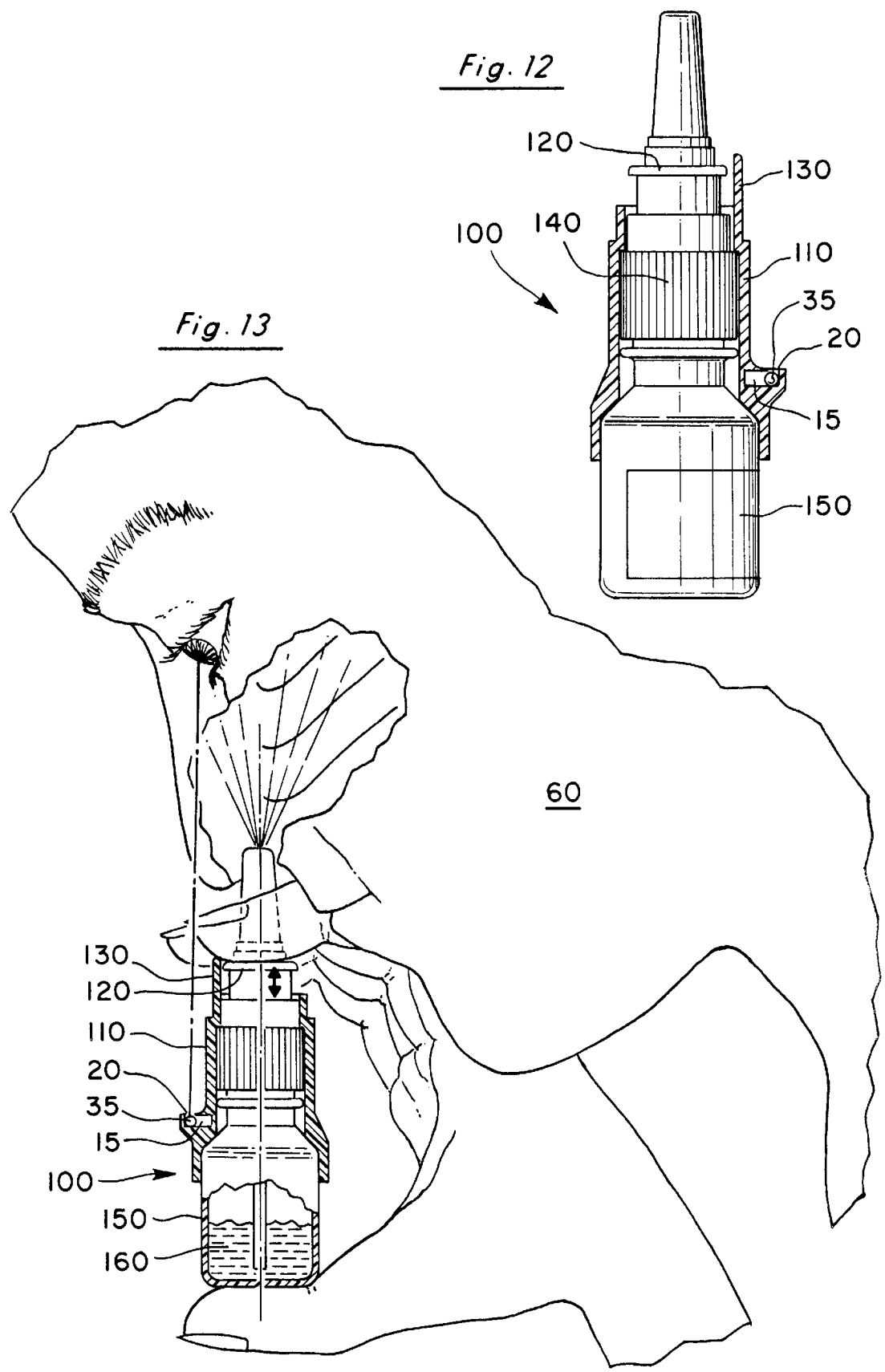

APPARATUS FOR INDICATING PROPER ORIENTATION FOR ORAL AND NASAL INHALERS

RELATED APPLICATION

The present application is based on the Applicants' U.S. Provisional patent application 60/030,212 filed on Nov. 5, 1996.

BACKGROUND OF THE INVENTION

1. Field of the Invention

The present invention relates generally to the field of oral and nasal inhalers. More specifically, the present invention discloses a device for improving medication compliance by patients utilizing medication inhalers by providing visual, audible, and tactile indication of proper inhaler orientation, audible and tactile indication of proper inhaler shaking, and improved leverage and comfort during the process of depressing the oral metered dose medication vial.

2. Statement of the Problem

Inhalation has long been known as a method for administering medicines for distribution and absorption into the airways, lungs, and nasal passages. Inhalation devices are the predominant medication delivery system for treating asthma and other respiratory disorders such as chronic bronchitis. A variety of inhalation devices are commercially available for this purpose, and with each device liquid or powdered medication preparations are introduced by the patient into his or her respiratory system where the medications are finely distributed throughout either the bronchial airways and alveoli or nasal sinus cavities.

Hand-held metered dose inhalers are the preferred method of treatment for most common respiratory ailments, allowing the patient to inhale medication when needed. It has been reported that a large majority of patients using inhalers do so incorrectly. Creer et al., "Medication Compliance and Asthma: Overlooking the Trees Because of the Forest," *Journal of Asthma*, 33(4) 203–211(1996), Hampson et al., "Reduction in Patient Timing Errors Using a Breath-Activated Metered Dose Inhaler," *Chest* 106: 462 (1994)]. It is commonly appreciated in the medical profession that many patients do not obtain the full benefit of inhaled medications because their inhalation technique is incorrect. Indeed, getting patients to correctly use inhalers is a major problem, especially with patients who use their inhaler infrequently. In general, it is necessary for a person utilizing an oral inhaler to properly align the mouthpiece with their mouth and throat and inhale properly and deeply while dispensing the medicament. With a nasal inhaler it is important to align the inhaler and nose to direct the spray towards the back of the nose into the nasal cavity. Although simple in description, the operation of both oral and nasal inhalers is more often mis-practiced with the unfortunate consequence that some patients may stop taking their medications because they are not seeing any appreciable benefit. Additionally many patients, having failed to obtain expected benefits through prescribed usage, will overuse the inhaler, subjecting themselves to increased risks of side effects caused by a higher than normal dose, such as fungal infections of the mouth and throat with inhaled steroids as well as nervous system over stimulation due to excessive dosing with beta agonists (e.g. albuterol).

Proper use of an oral inhaler requires seven recommended steps of (1) correct assembly of the parts, (2) shaking of the inhaler before use, (3) slow exhalation of tidal volume, (4) correct positioning of the inhaler at the mouth or nose, (5) activation immediately after initiation of inhalation, (6) slow, deep inhalation, and (7) breath holding for 6 to 10 seconds. In one reported study, Amirav et al., "What do Pediatricians in Training Know About the Correct Use of Inhalers and Spacer Devises?" *J. Allergy Clin. Immunol.* 94: 669 (1994), pediatric residents were asked to demonstrate the correct use of inhalers as if they were instructing patients. The most common errors included not shaking the inhaler (only 18% of the residents did it correctly) and insufficient breath holding (28% of the residents did it correctly). In November, 1996 (American College, Allergy, Poster Session) a study by Wanderer et al., inhaler technique was observed in 67 asthmatic patients who had not been seen in private allergy practice for at least one year. The most common errors included not shaking the device before use (40%), improper positioning of the inhaler vertically (45%), coordination problems (31%), and insufficient breath holding (25%). Together these studies underscore the need for developing methods and engineering controls to improve correct inhaler technique.

Of the problems reported, two of the most significant are not shaking the inhaler prior to use and improper vertical orientation. Since the active medication and aerosol propellant are frequently in suspension within the vial, it is necessary to shake the mixture prior to use. Shaking is necessary to insure that settling of the aerosol components does not result in an improper dose of the active medication. This is particularly true in cases where the inhaler is not used for days at a time. The second factor of concern is proper vertical orientation of the inhaler and the patients head. As with most propellant systems, if the inhaler is not properly oriented when activated the user may dispense an improper mix of propellant and active medication, resulting in improper dosing. Further, during inhalation, improper orientation of the inhaler may also result in impaction of the medication to the tongue, roof of the mouth, side of the mouth, sides of the nose, or throat. Improper orientation of the user's head in relation to the orientation of the inhaler is also problematic. When a person's head is tilted forward, human physiology is such that the airway to and from the lungs becomes more constricted, significantly restricting the flow of air to and from the lungs. Restricting the air flow is not desirable with the use of oral inhalers as it reduces distribution of the dose of medication throughout the bronchial passageways.

In addition, some types of inhalers will not function properly unless the inhaler is held in a substantially vertical orientation. For example, the Maxair Autohaler includes a valve mechanism that only releases medication when the patient exerts an adequate inhalation effort to ensure that the medication will be inhaled into the lungs. However, this valve mechanism is sensitive to orientation, and will not function unless held in a substantially vertical orientation.

Improper orientation during use may be attributed primarily to several factors. First, patients may not be aware or not recall the proper orientation of the inhaler. Second, it is difficult to judge the orientation of an inhaler located directly in front of the person's nose. In addition, some patients experience difficulty depressing the aerosol vial, especially patients with weak hands such as with arthritis or other disabilities. To date, the traditional approach for improving inhaler technique has involved the implementation of educational programs to teach health care workers and patients about the proper use of inhalers. This approach is time consuming and requires expensive human resources. Moreover, some patients use their inhalers sporadically with long intervals between use. Lack of practice and memory recall contribute to improper use of inhalers such that patients need to be reinforced periodically on the proper use of these devices. To aid in reinforcing and teaching technique, several inhalation devices have been developed to help insure proper use and provide feedback, including the following:

| Inventor | Patent No. | Issue Date |
|---|---|---|
| Fowler | 3,404,681 | October 8, 1968 |
| Kistler | 4,291,688 | September 29, 1981 |
| Wass et al. | 5,349,945 | September 27, 1994 |
| Del Bon et al. | 5,355,873 | October 18, 1994 |
| Mishelevich | 5,363,842 | November 15, 1994 |

Fowler discloses a general example of an oral inhaler aerosol dispenser device for administering a medication by inhalation. To aid in encouraging the inhaler user to inhale during administration of a measured dosage, air passage through the inhaler's housing is only possible after the aerosol container has been depressed. Following placement of the inhaler within the mouth, the user inhales and produces a partial vacuum. Depressing the aerosol container dispenses a metered amount of medication and at the same time allows air to flow through a gap created between the delivery tube and the aerosol container into the mouthpiece.

Kistler discloses an oral inhalation device of the type adapted to receive and locate an aerosol container designed to administer a multiplicity of metered doses. To aid in achieving proper inhalation during dose administration, the inhaler device contains an audible signal generating means in the air passageway within the inhaler hosing. When the patient properly inhales through the inhaler, a confirming whistle sound is produced. Failure to inhale at a sufficient rate, or exhalation, will not produce the confirming whistle.

Wass et al. discloses an oral inhaler of the aerosol dispenser type for use with an aerosol vial. Within the dispenser is located an indicator assembly that reports the number of doses dispensed or remaining in the aerosol vial.

Del Bon et al. discloses an oral inhalation device for use with an aerosol vial in which the air flow through the inhaler may be variably restricted. To insure against accidental firing of the aerosol vial in the inhaler, as well as proper inhalation by the using patient, a positive locking unit is employed. Placing the mouthpiece of the device within the mouth, the using patient begins to inhale. The flow rate of air through the inhaler may be adjusted to accommodate patients of different age and lung capacity. The reduced air flow through the inhaler results in a suction that disengages the locking mechanism, allowing the aerosol vial to be depressed, thus dispensing the medication.

Mishelevich discloses an oral inhaler device for use with an aerosol vial. This inhaler device detects, reports, and records information regarding its use, such as how much air is inhaled through the inhaler housing during use, the time involved for inhalation, and when in this time course the aerosol vial was depressed. This device uses a microprocessor to compare actual time to target time as well as recording the history of usage for later report to a healthcare professional. Immediate response of the dosage administered, air inhalation and other information are also provided to the user on an LCD display.

3. Solution to the Problem

None of the above prior art references show a device that provides immediate, easy to see, visual as well as audible and tactile indication of proper inhaler orientation during use. Additionally none of the prior art references provide the inhaler user with an audible and tactile confirmation of proper inhaler shaking prior to use. Further none of the prior art references address the difficulty experienced by some patients in effectively depressing the aerosol vial. The present invention overcomes these shortcomings associated with the prior art systems. With the mouthpiece positioned at or within the mouth, or the spray tip within the nostril, the user must properly position their head and the inhaler in the correct vertical orientation. Correct orientation will cause an indicator ball to become visible to the user. The user with impaired vision or under dim light conditions will know how to hold the inhaler in the correct position based on tactile and auditory feedback of the ball moving to the front of the tube in the cap. Shaking the inhaler prior to use causes the indicator ball to rattle, thereby serving as a audible reminder. In addition, the user can feel the vibration of the ball ratting inside the inhaler which also serves as a reminder to shake the inhaler. The preferred embodiment of the present invention when applied to oral inhalers includes an ergonomic cap having a top surface curved to fit the contour of the first finger knuckle. The ergonomic shape of the cap reduces the force required to depress the aerosol vial, and makes the inhaler easier to use. When applied to nasal inhalers, the preferred embodiment of the present invention includes an orientation guide preventing the nasal pump from rotating out of alignment with the visual indicator.

SUMMARY OF THE INVENTION

This invention provides an apparatus to insure proper positioning during use of an inhaler, as well as providing an audible rattle to aid in remembering to shake the inhaler prior to use. The present invention uses a visual indicator contained within a housing attached to the inhaler. Most commonly this visual indicator is comprised of an indicator ball confined inside a substantially horizontal tube within the inhaler housing. For example, the tube may be formed into a cap placed on the aerosol vial of the inhaler or affixed to the side of the inhaler housing. One end of the tube is exposed within the user's field of view. The indicator ball remains out of view within the inhaler housing unless the inhaler is held in a substantially vertical orientation. When proper vertical orientation is achieved, the indicator ball rolls to the exposed end of the tube and is visible to the user. Persons using the inhaler under dim light conditions and a visually impaired user can also determine proper vertical positioning of the inhaler by tactile sensation and sound of the ball moving to the exposed end of the tube. Shaking the inhaler prior to use causes the indicator ball to rattle within the tube producing an audible rattle. The event of shaking the inhaler and hearing the rattle provides the user with a reinforced memory to shake the inhaler prior to use. In addition, the user can be reminded to shake the inhaler by sensing vibration from the movement of the ball inside the tube. In the preferred embodiment as applied to oral inhalers, the indicator ball and tube are placed within an ergonomic cap seated on the upper end of the aerosol vial of the inhaler. When the inhaler mouthpiece is placed in the mouth or adjacent to the mouth, the cap and the exposed end of the tube are proximate to the bridge of the nose, directly between the user's eyes. The cap can be equipped with a top surface curved to fit the contour of the first finger knuckle. In the preferred embodiment as applied to nasal inhalers, the indicator ball and tube are placed within a collar housing placed upon the inhaler. When the spray tip is placed within a nostril, the exposed end of the tube is directly below the nose in clear view.

A primary object of the present invention is to provide immediate visual, audible and tactile confirmation that the orientation of the inhaler is correct for use.

Another object of the present invention is to provide an audible sound and tactile sensation when the inhaler is shaken prior to use, such a sound and tactile sensation facilitating memory to shake the inhaler in the future before use.

Another object of the present invention is to reduce finger stress in operating the oral inhaler by providing a comfortable point of finger contact that improves leverage, facilitating more consistent use by patients.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 5 is a side cross-sectional view of the ergonomic cap depicting the location and orientation of the tube and indicator ball within the ergonomic cap.

FIG. 6 is a front perspective view of the ergonomic cap removed from the inhaler.

FIG. 7 is a side view of the ergonomic cap removed from the inhaler.

FIG. 12 is a side cross-sectional view of the nasal inhaler with an indicator ball and tube located within the collar housing.

FIG. 13 is a side view of the nasal inhaler with an indicator ball and tube in the collar housing in use by a person properly positioning the inhaler such that the indicator ball is in view.

DETAILED DESCRIPTION OF THE INVENTION

Figure 1:
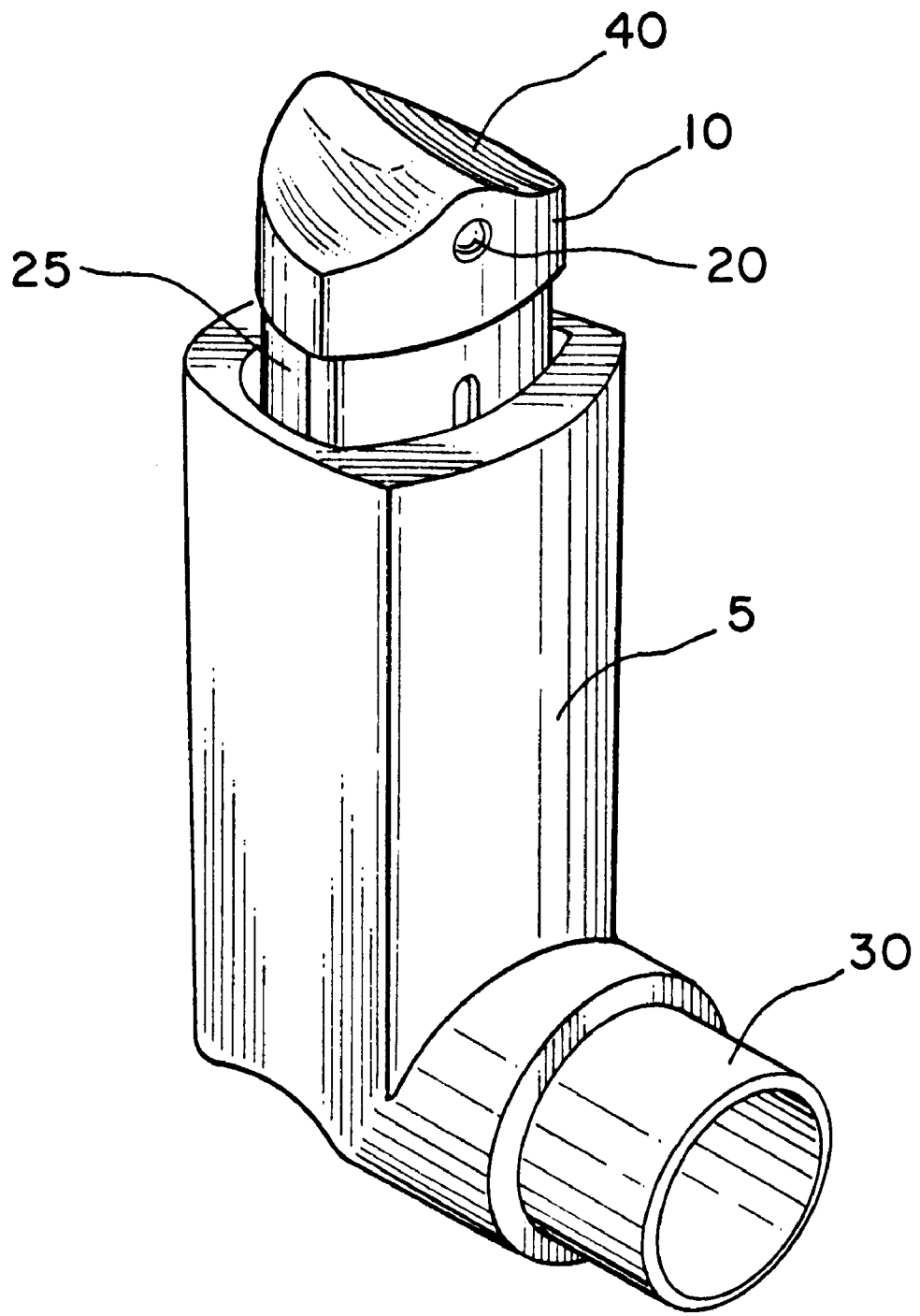
FIG. 1 is a perspective side view of the oral inhaler with an indicator ball and tube located in the ergonomic cap.
Figure 3:
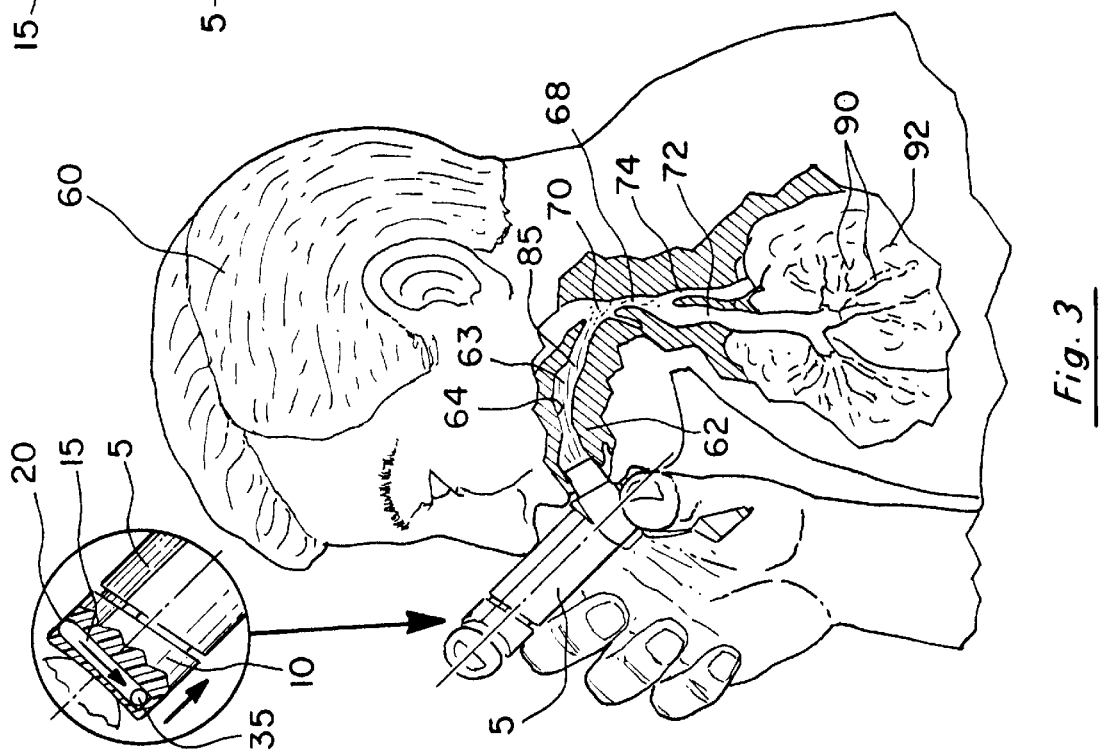
FIG. 3 is a side cross-sectional view of the oral inhaler with an indicator ball and tube in the cap in use by a person improperly positioning the inhaler such that the indicator ball is not in view.

Turning to FIG. 1, a perspective side view is shown of an oral inhaler 5 incorporating the present invention. The inhaler 5 generally includes an ergonomic cap 10, an aerosol vial 25 containing medication, and a mouthpiece 30. In the preferred embodiment as depicted in FIG. 1, the housing for the inhaler 5 includes an ergonomic cap 10 mounted on top of the aerosol vial 25. As shown in the cross-sectional view of the cap 10 provided in FIG. 5, the visual indicator consists primarily of a horizontal tube 15 extending rearward from the front of the cap 10. An indicator ball 35 rolls within the tube 15. The front end 20 of the tube 15 is visually exposed through the front surface of the cap 10. If orientation of the inhaler 5 is not sufficiently vertical, the indicator ball 35 will remain in the tube 15 within the cap 10 and will not be visible, as illustrated in FIGS. 3 and 5. When vertical orientation is achieved, the indicator ball 15 will roll forward to the front end 20 of the tube 15 where it is visible to the user, as shown in FIG. 4.

Figure 2:
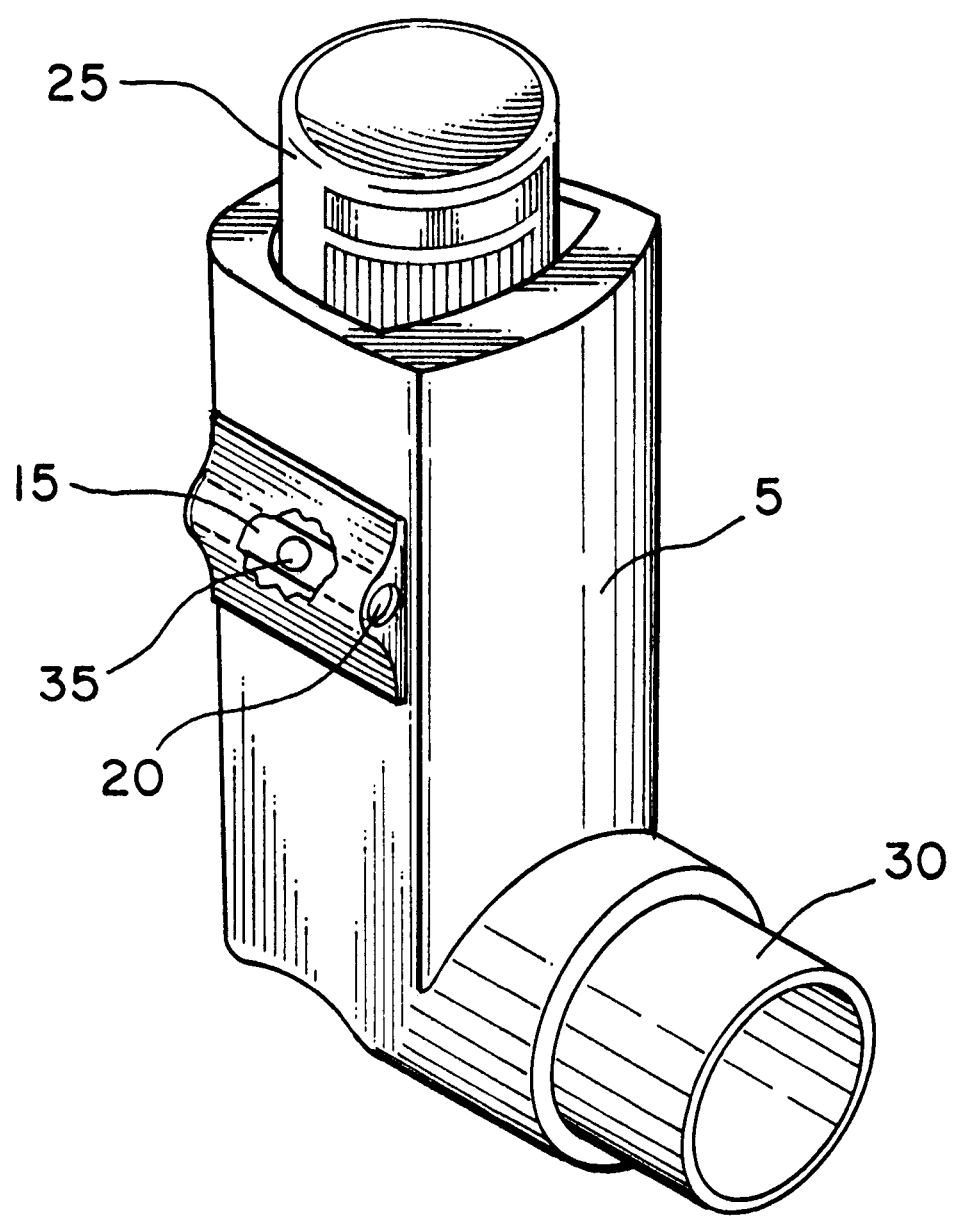
FIG. 2 is a perspective side view of the oral inhaler with an indicator ball and tube located in the side housing of the inhaler.

FIG. 2 provides a perspective view of an alternative embodiment of the present invention in which the tube 15 is housed in a widened section of the side of the housing for the inhaler 5. Here again, the indicator ball 35 rolls along the horizontal tube 15. The ball is only visible at the exposed front end 20 of the tube 15 when the inhaler 5 is held in a substantially vertical orientation.

In the preferred embodiment shown in the drawings, the exposed end 20 of the tube 15 has a constricted opening with a diameter that is slightly smaller than the diameter of the indicator ball 35 to prevent the indicator ball 35 from falling out of the tube 15. Placing the indicator ball 35 within the tube may be facilitated by leaving the rear end of the tube 15 open, to be sealed after the ball is inserted. In other configurations, the indicator ball 35 can be manually popped through the constricted opening to introduce the ball 35 into the tube 15 during initial assembly of the cap 10. The ball 35 can also be popped through a smaller opening on the interior surface of the tube 15 which is located on the underside of the cap 10. The exposed end 20 of the tube 15 can remain open or be sealed to provide a window or transparent bubble for viewing the indicator ball 35.

Figure 4:
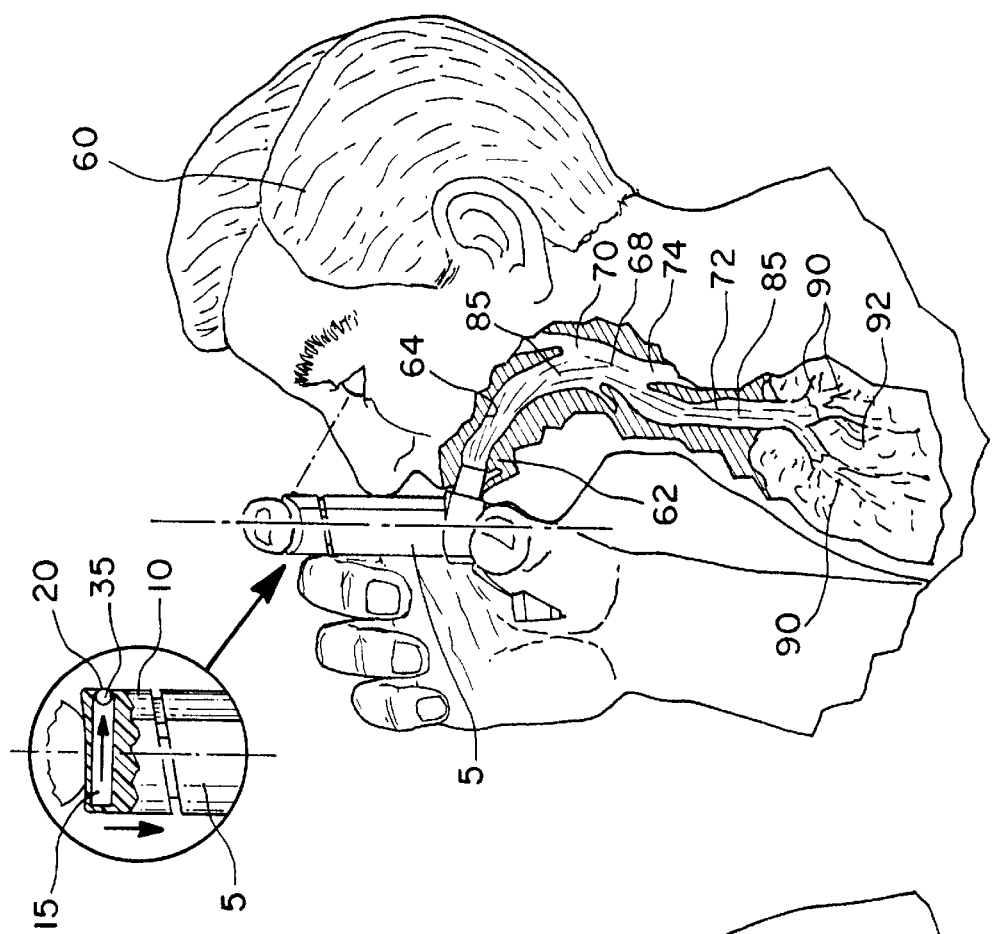
FIG. 4 is a side cross-sectional view of the oral inhaler with an indicator ball and tube in the cap in use by a person properly positioning the inhaler such that the indicator ball is in view.

FIGS. 3 and 4 depict side cross-sectional views of an inhaler 5 being used by a patient 60 in an improper position and the proper position, respectively. In FIG. 3, the patient's head 60 and the inhaler 5 are tilted forward which constricts the airway and impedes normal breathing. The medication is more likely to be applied to the tongue 62, roof 64 or side of the mouth 63, or throat 68, rather than reaching the bronchial passageways 90 within the lungs 92. Further, an improper proportion of medication and propellant may be dispensed from the aerosol vial 25 if the inhaler is not oriented vertically. Additionally, when the user bends his head forward the tissue structures in the mouth and throat 68, such as the tongue 62, larynx 70, trachea 72, and esophagus 74 are compressed against one another. Compression of the larynx 70 and trachea 72 constricts the passage of air to and from the lungs 92 and reduces the amount of medication 85 reaching the bronchial passageways 90 within the lungs 92. In the improper position shown in FIG. 3, the indicator ball 35 is not visible at the exposed end 20 of the indicator tube 15.

In contrast, the correct position for the inhaler 5 and head 60 are illustrated in FIG. 4. Proper position of the user's head 60 is as important as the orientation of the inhaler 5 itself. When the head 60 is held upright and tilted slightly back, the patient's airway is fully open. In this vertically upright position the mouthpiece 30 of the inhaler 5 device is properly aligned to direct the medication 85 through the mouth, over the tongue 62, down the throat 68, and into the bronchial passageways 90 within the lungs 92. When the inhaler 5 is properly oriented vertically, and the user's head is properly vertically upright, the end of the aerosol vial 25 is directly between the users eyes, proximate to the nose. In this position the indicator ball 35 is very easy to see at the exposed end of the tube 15, as shown in FIG. 4. In addition, there is audible and tactile indication of the ball 35 moving to the front of the tube 15 as a means of ensuring proper vertical orientation of the inhaler.

It should be noted that improper head and inhaler orientation most often occur together. If the user simply orients his head as bent forward, the passage of air to and from the lungs 90 is not as fully open as if the head is tilted back more vertically, to move the tongue 62, larynx 70 and trachea 72 apart. Given the physical design of the mouthpiece on most inhalers, it is not physically possible to have the inhaler mouthpiece within the user'mouth, and the inhaler in proper vertical orientation while the user has his head bent forward. Proper orientation of the head is a natural result of properly orienting the inhaler 5 so that the indicator ball 35 appears. As the user orients the inhaler 5, the user will move his head as well to both maintain contact with the mouthpiece and to avoid pressing the inhaler into his nose.

It should be expressly understood that other visual indicative means could be substituted for the tube shown in the drawings, e.g., parallel rails, tracks, or other means of confining the indicator ball 35 to move along a channel between a concealed position and an exposed position. Although depicted as horizontal in the figures, it is also to be understood that the tube 15 could be positioned with a slight angle of inclination from horizontal.

The aerosol vial 25 may contain a suspension of propellant and medication that must be shaken vigorously to ensure a proper mix of both components prior to aerosolization. The vibration of the moving ball 35 inside the tube 15 serves to remind the user to shake the inhaler prior to use. To achieve a rattling sound, the indicator ball 35 may be formed of metal or plastic. The indicator ball can have a bright color to enhance visibility. It may further be desirable to have a second ball 36 located behind the indicator ball 35 within the tube 15, as shown in FIG. 5. When shaken, this additional ball 36 will knock against the indicator ball 35 to produce a louder sound than a single ball rattling alone within the tube 15. In addition, the movement of the ball 35 and additional ball 36 inside the tube 15 will cause vibration which will also serve as a tactile means to remind the user to shake the inhaler.

Figure 8:
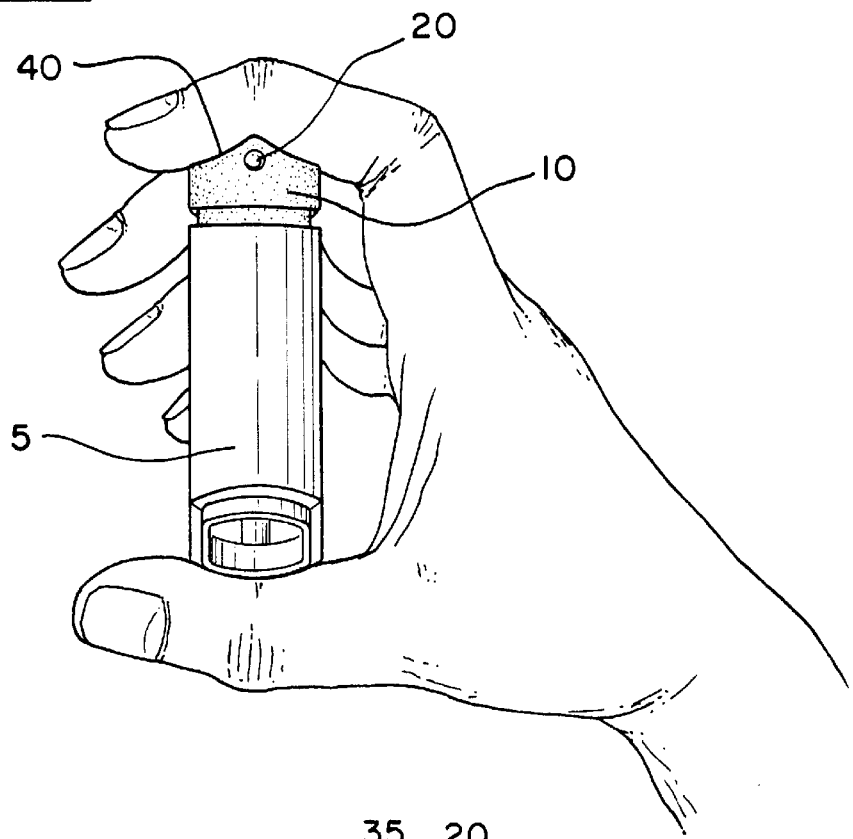
FIG. 8 is a front view of the inhaler showing proper finger placement on the ergonomic cap.

The preferred embodiment shown in FIGS. 1 and 3–8 incorporates the indicator ball within an ergonomic cap 10. This ergonomic cap 10 is placed on the upper end of the aerosol vial 25. The upper end of the aerosol vial 25 is where the user would ordinarily place his or her finger to depress the aerosol vial 25 when dispensing medication. Current manufacturing methods for inhaler aerosol vials result in a concave surface of this upper end of the vial that does not conform naturally to the shape of a human finger. With current inhalers, the finger must be placed flat against the upper concave end of the aerosol vial 25 which imparts significant stress on the first finger joint. As depicted in FIGS. 1, 6 and 7, the top surface 40 of the ergonomic cap 10 has been formed to provide a surface curved for the inside of the first finger knuckle. Specifically, this surface is achieved by placing two concave oval surface sections adjacent to one another. These surface sections are slightly tilted such that their edges at point of union are raised in elevation above the trailing edges. A pronounced horizontal ridge running along the point of union completes the ergonomic structure. The improved fit between the user's finger and cap 10 allows for improved comfort and leverage during the operation of depressing the aerosol vial 25 as shown in FIG. 8. The shape of the ergonomic cap 10 is additionally beneficial in insuring that finger placement is proper and consistent from use to use.

Figure 9:
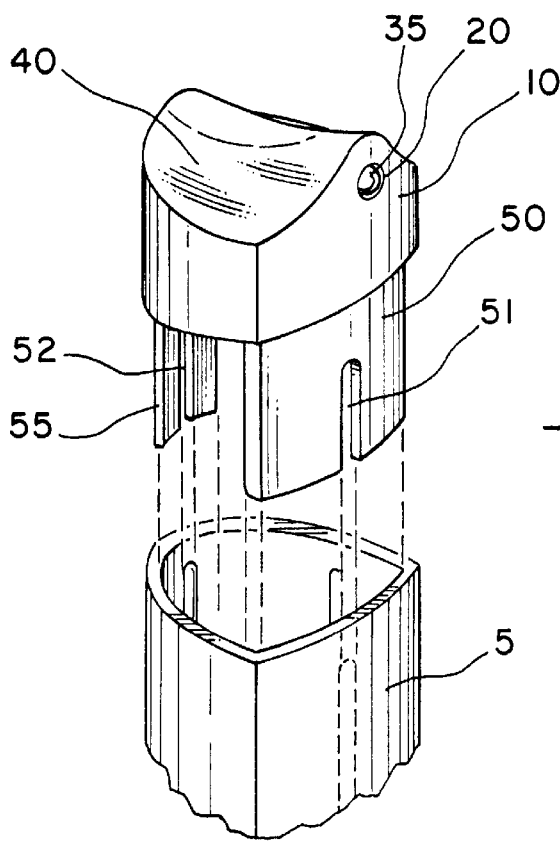
FIG. 9 is an exploded view of the ergonomic cap.

The cap 10 is held on the aerosol vial 25 by front and rear tabs 50, 55 extending downward from the cap as illustrated in FIGS. 6 and 7 that provide a friction fit against the sides of the aerosol vial 25. Adhesive could also be used to insure a tight hold of the ergonomic cap 10 to the aerosol vial 25. The cap 10 and its front and rear tabs 50, 55 also help to ensure that the aerosol vial 25 is properly aligned in the inhaler housing and that the dispenser valve of the aerosol vial 25 will properly engage the port behind the mouthpiece 30 of the inhaler 5. Shown in FIGS. 6 and 9, groves 51 and 52 serve as a guide and means for proper assembly and orientation. During assembly, the cap 10 is placed upon the aerosol vial 25, which in turn is inserted into the inhaler housing. Groves 51 and 52 mesh with vertical casting ridges within the inhaler housing. Additionally, when the front and rear tab 50 and 55 with groves 51 and 52, are properly aligned with the casting ridges within the housing, lateral movement of the aerosol vial is restricted while vertical movement is unrestricted. The cap 10 also provides an improved grip for removing the aerosol vial 25 from the inhaler 5.

It is sometimes difficult for a patient to determine whether an aerosol vial 25 is completely empty after it has been used a number of times. The "float" test that many patients use involves removing the aerosol vial 25 from the inhaler housing and placing it in a cup of water. The vial 25 will sink if it still contains doses of medication and will float if it is empty. The cap 10 can be produced from a floatable plastic material that will provide an easier method for determining fullness of the aerosol vial. An empty vial will cause the cap and vial to float horizontally across the surface of the water. A non-empty vial will float vertically beneath the cap such that the cap and vial are perpendicular to the water surface. Thus it will be easier to retrieve the cap and vial from the cup of water after the fullness test.

Currently there are a wide variety of oral inhalation devices manufactured for use. The age and size of patients utilizing inhalation devices is also quite varied. In consideration of these facts it is to be understood that the visual indicator device such as the described indicator ball 35 and tube 15 can be placed anywhere within the inhaler housing without appreciable affect to the present invention. When the indicator ball 35 and tube 15 are not placed within a cap 10, the use of an ergonomic cap is still intended for the benefits of insuring proper and consistent finger placement.

The indicator ball 35 and tube 15 address proper vertical orientation in only one plane. It is to be understood that a sealed fluid-filled tube with an air bubble (similar to a carpenter's bullet level) or other forms of visual indicators could be substituted for the tube 15 and indicator ball 35. A slight deviation to the patient's right or left is not likely to significantly effect the use of the inhaler in most situations. However, a combination of tube and ball indicators, two bullet levels, a circular fluid filled disk with an air bubble and centering mark (commonly known as a bulls-eye level), or other indicative devices may be employed where precise orientation in more than one plane is desired. It should also be understood that while this invention directly pertains to the use of inhalers 5 using aerosol vials 25 to dispense medication, the present invention may be readily applied to non-aerosol powder or liquid inhalers.

Figure 10:
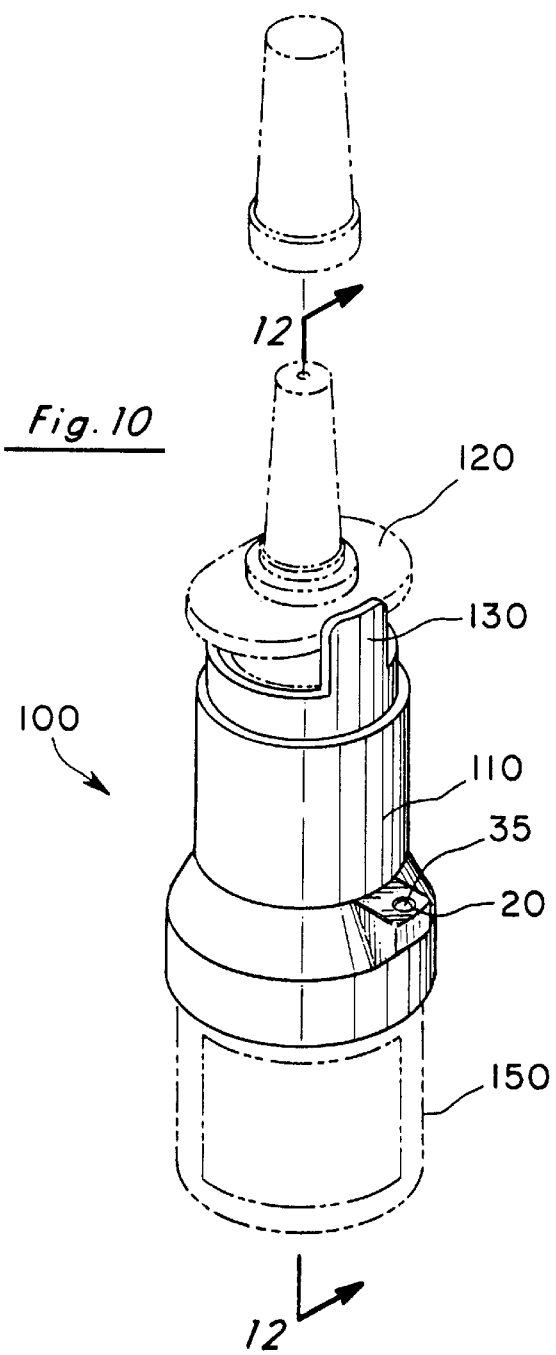
FIG. 10 is a perspective view of a nasal inhaler with an indicator ball and tube located in the collar housing.
Figure 11:
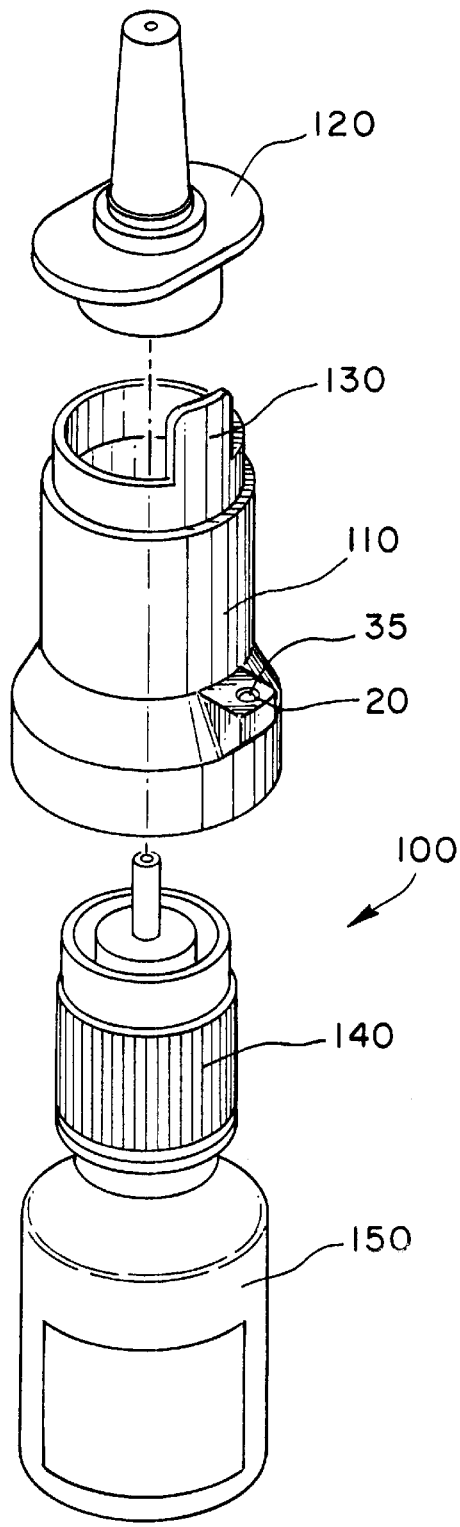
FIG. 11 is an exploded view the a nasal inhaler with an indicator ball and tube in the collar housing.

While the above discussion has concentrated largely on application of the present invention to oral inhalers, it is to be understood that the same teaching may be applied to nasal inhalers. Orientation of the head and inhaler is critical for proper use of nasal inhalers, just as with oral inhalers. FIGS. 10 and 11 present perspective views of a nasal inhaler 100 incorporating the present invention. The nasal inhaler 100 generally includes a collar housing 110, a spray tip with finger pads 120, and a rotation limiting extension 130. In the preferred embodiment as depicted in FIGS. 10–13 the collar housing 110 for the inhaler 100 includes the visual indicator comprised of a horizontal tube 15 and indicator ball 35, as described above. The cross-sectional views provided in FIGS. 12 and 13 clearly illustrate the location of the tube 15 and ball 35 within the collar housing 110. Only when the user has properly oriented the nasal inhaler will the indicator ball roll into view at the opening 20.

As currently manufactured, nasal inhalers are comprised of a pump action spray unit 140 screwed atop a medication vial 150. The interior of the collar housing 110 is designed to mesh with the ridges present on the pump action spray unit 140, and thereby prevents rotation of the collar housing 110. To prevent rotation of the spray tip with finger pads 120, a rotation limiting extension 130 protrudes upwardly from the collar housing 110. By preventing rotation of the spray tip with finger pads, proper and consistent holding and orientation of the inhaler and head may be achieved with each use.

As depicted in FIG. 13. The user must tilt their head forward while maintaining the nasal inhaler 100 in a substantially vertical orientation. This positioning insures that the medication will be dispersed into the nasal cavity and not simply impact into the roof of the nose. Additionally, as these nasal inhalers most often contain liquid medication, proper vertical orientation of the inhaler is essential to insure that the liquid medication 160 is drawn through the pump spray unit 140. Constriction of the airway to and from the lungs is not as great an issue as with oral inhalers, as here the medication is intended for the nasal and sinus cavities. The functioning of the ball 35 and tube 15 as a tactile and audible indicator of orientation and reminder to shake the device are identical to their use with oral inhalers 5.

The above disclosure sets forth a number of embodiments of the present invention. Other arrangements or embodiments, not precisely set forth, could be practiced under the teachings of the present invention and as set forth in the following claims.

We claim:

1. An apparatus for indicating proper orientation of an inhaler by a patient comprising:
    a housing for attachment to an inhaler;
    a visual indicator; and
    means for enabling movement of said visual indicator relative to said housing between a visible position within the visual field of the patient when an inhaler is held in the proper orientation, and a concealed position when an inhaler is not held in the proper orientation.

2. The apparatus of claim 1 wherein said means for enabling movement of said visual indicator comprises a tube having a concealed portion within said housing and an exposed portion visible from outside said housing.

3. The apparatus of claim 2 wherein said visual indicator comprises a ball rolling within said tube.

4. The apparatus of claim 3 wherein said ball within said tube produces an audible rattling sound when the inhaler is shaken.

5. The apparatus of claim 3 wherein said ball produces a tactile indication when said ball moves to said exposed portion of said tube.

6. The apparatus of claim 3 wherein said exposed portion of said tube further comprises an opening having a diameter smaller than the diameter of said ball.

7. The apparatus of claim 1 wherein said housing further comprises a cap for attachment to the top of an inhaler in the patient's field of view when the inhaler is in use.

8. The apparatus of claim 7 wherein said means for enabling movement of said visual indicator comprises a tube having a concealed portion within said cap and an exposed end within the patient's field of view.

9. The apparatus of claim 7 wherein said cap further comprises an ergonomic top surface contoured for the patient's finger.

10. The apparatus of claim 1 wherein the inhaler is a nasal inhaler having a spray tip, wherein said housing further comprises a collar for extending about the spray tip of an inhaler, and wherein said means for enabling movement of said visual indicator comprises a tube having a concealed portion within said collar and an exposed end within the patient's field of view.

11. The apparatus of claim 10 wherein said collar further comprises means for preventing rotation of said collar about said spray tip.

12. An apparatus for indicating proper orientation of an inhaler by a patient comprising:
    a housing for attachment to an inhaler;
    a tube having a concealed portion within said housing and an exposed portion visible to the patient; and
    a visual indicator moving to a visible position within said exposed portion of said tube when an inhaler is held in the proper orientation, and moving to a concealed position within said concealed portion of said tube when an inhaler is not held in the proper orientation.

13. The apparatus of claim 12 wherein said visual indicator comprises a ball rolling within said tube.

14. The apparatus of claim 13 wherein said ball produces an audible rattling sound when the inhaler is shaken.

15. The apparatus of claim 13 wherein said ball produces a tactile indication when said ball moves to said exposed portion of said tube.

16. The apparatus of claim 13 wherein said exposed portion of said tube further comprises an opening having a diameter smaller than the diameter of said ball.

17. The apparatus of claim 13 wherein said ball within said tube produces an audible rattling sound when said apparatus is shaken.

18. The apparatus of claim 12 wherein said housing further comprises a cap for attachment to the top of an inhaler in the patient's field of view when the inhaler is in use, said cap containing said tube and visual indicator.

19. The apparatus of claim 18 wherein said cap further comprises an ergonomic top surface contoured for the patient's finger.

20. The apparatus of claim 12 wherein the inhaler is a nasal inhaler having a spray tip, wherein said housing further comprises a collar for extending about the spray tip of an inhaler, and wherein said concealed portion of said tube is within said collar.

21. The apparatus of claim 20 wherein said collar further comprises means for preventing rotation of said collar about said spray tip.

22. An apparatus for indicating proper orientation of an inhaler by a patient comprising:

a cap for attachment to the top of an inhaler;

a tube having a concealed portion within said cap and an exposed end extending through said cap within the field of view of the patient; and a ball moving to a visible position within said exposed end of said tube when an inhaler is held in the proper orientation, and moving to a concealed position within said concealed portion of said tube when an inhaler is not held in the proper orientation.

23. The apparatus of claim 22 wherein said ball produces an audible rattling sound when the apparatus is shaken.

24. The apparatus of claim 22 wherein said exposed end of said tube further comprises an opening having a diameter smaller than the diameter of said ball.

25. The apparatus of claim 22 wherein said cap further comprises an ergonomic top surface contoured for the patient's finger.

* * * * *